(12) United States Patent
Green et al.

(10) Patent No.: US 9,829,465 B2
(45) Date of Patent: Nov. 28, 2017

(54) ABSORPTION MODE FT-IMS

(71) Applicant: Micromass UK Limited, Wilmslow (GB)

(72) Inventors: Martin Raymond Green, Bowdon (GB); Keith George Richardson, High Peak (GB); David J. Langridge, Macclesfield (GB)

(73) Assignee: Micromass UK Limited, Wilmslow (GB)

( * ) Notice: Subject to any disclaimer, the term of this patent is extended or adjusted under 35 U.S.C. 154(b) by 66 days.

(21) Appl. No.: 15/078,319

(22) Filed: Mar. 23, 2016

(65) Prior Publication Data

US 2016/0284530 A1    Sep. 29, 2016

(30) Foreign Application Priority Data

Mar. 24, 2015  (GB) .................... 1504938.0

(51) Int. Cl.
  *G01N 27/62*  (2006.01)
  *H01J 49/02*  (2006.01)
  *H01J 49/00*  (2006.01)

(52) U.S. Cl.
  CPC ........ *G01N 27/622* (2013.01); *H01J 49/0036* (2013.01)

(58) Field of Classification Search
  CPC ..................... G01N 27/622; H01J 49/0036
  See application file for complete search history.

(56) References Cited

U.S. PATENT DOCUMENTS

| 4,633,083 | A  | * | 12/1986 | Knorr | .............. | G01N 27/622 |
|||||||250/282|
| 6,580,068 | B1 |   | 6/2003  | Tarver et al. | | |
| 8,853,620 | B2 |   | 10/2014 | Lange et al. | | |
| 2005/0178961 | A1 | * | 8/2005 | Beu | .................. | H01J 49/38 |
|||||||250/291|
| 2011/0240841 | A1 | * | 10/2011 | Lange | ............. | H01J 49/0036 |
|||||||250/282|
| 2012/0235032 | A1 |   | 9/2012 | Goebel et al. | | |

OTHER PUBLICATIONS

Craig et al., "Dispersion versus Absorption (DISPA) method for Automatic Phasing of Fourier Transform Ion Cyclotron Resonance Mass Spectra", Rapid Comm. In Mass Spec., vol. 1, No. 2, pp. 33-37, 1987.
Hilger et al., "Absorption Mode Fourier Transform Electrostatic Linear Ion Trap Mass Spectrometry", Anal. Chem., vol. 85, No. 17, pp. 8075-8079, 2013.
Qi et al., "Phase Correction of Fourier Transform Ion Cyclotron Resonance Mass Spectra Using MatLab", Journal of the American Soc. for Mass Spec., vol. 22, No. 1, pp. 138-147, 2011.

(Continued)

*Primary Examiner* — Jason McCormack
*Assistant Examiner* — Eliza Osenbaugh-Stewart
(74) *Attorney, Agent, or Firm* — Diederiks & Whitelaw, PLC

(57) ABSTRACT

A method of Fourier transform ion mobility spectrometry is disclosed wherein an absorption spectrum of the complex spectral data is used to determine the ion mobilities of ions.

15 Claims, 2 Drawing Sheets

(56) References Cited

OTHER PUBLICATIONS

Vining et al., "*Phase Correction for Collision Model Analysis and Enhanced Resolving Power of Fourier Transform Ion Cyclotron Resonance Mass Spectra*", Anal. Chem, vol. 71, No. 2, 460-467, 1999.
Knorr et al., "*Fourier Transform Ion Mobility Spectrometry*", Anal. Chem., vol. 57, pp. 402-406, 1985.
Knorr, "*Fourier Transform Time-of-Flight Mass Spectrometry*", Anal. Chem., vol. 58, pp. 690-694, 1986.
Szumlas et al., "*Phase-Resolved Detection in Ion Mobility Spectrometry*", Analytica Chimica acta, vol. 566, pp. 45-54, 2006.

\* cited by examiner

Voltage frequency (Hz)

ABSORPTION MODE FT-IMS

CROSS-REFERENCE TO RELATED APPLICATION

This application claims priority from and the benefit of United Kingdom patent application No. 1504938.0 filed on 24 Mar. 2015. The entire contents of this application are incorporated herein by reference.

FIELD OF THE INVENTION

The present invention generally relates to mass and/or ion mobility spectrometry and a spectrometer for performing such techniques. Embodiments of the invention relate to Fourier transform spectrometry and spectrometers.

BACKGROUND

Fourier transform time of flight and ion mobility (and other velocity dispersive analysis) are known. For example, see Knorr et al Anal. Chem. 1986. 58. 690-694 and Knorr, Hill Anal. Chem. 1985, 57, 402-406.

Fourier Transform Ion Mobility Spectrometry (FT-IMS) is a multiplexing technique in which ions are gated into and out of the ion mobility separator (IMS) cell by ion gates arranged at the ends of the IMS device. The gating signal that opens and closes the ion gate is generally identical on both ion gates and the frequency of the gating signal on each ion gate is swept with time. The duty cycle of the gating of the ion beam on both gates is generally set to 50%.

According to this arrangement, the amplitude of the output signal from the IMS device, for an ion of specific mobility, varies as a substantially triangular function that has a frequency that is characteristic of the ion's ion mobility. The ion signal may be measured as a function of the ion gate signal frequency. A Fourier transform is then applied to this data obtained in the ion gate modulation frequency domain so as to produce an ion mobility separation spectrum.

An advantage of FT-IMS is a much improved duty cycle compared to conventional atmospheric pressure ion mobility separation. In conventional atmospheric pressure ion mobility separation, ions are introduced into the drift region by rapidly opening and closing an ion gate once per IMS separation cycle. Typical gating times are in the order of 100 micro-seconds, whereas typical drift times through the IMS device are in the order of 100 milli-seconds, thus leading to a duty cycle in the order of 0.1%.

FT-IMS also has advantages over sub-atmospheric RF confined IMS techniques. In sub-atmospheric RF confined IMS devices ions are intermittently pulsed into the IMS device. In order to improve the duty cycle, between pulses when ions are not being admitted into the IMS device, the ions may be accumulated in an ion trapping region upstream of the IMS device. However, if the ion flux towards the IMS device is high then the charge density in the ion trapping region, or in the IMS device, may become high and the resulting space-charge effects may cause a loss of signal or distortions in the drift times of ions through the IMS device. These problems may be avoided in FT-IMS techniques because gating frequency allows the device to receive a continuous ion beam and operate with a relatively high duty cycle, without the need to store ions in an upstream ion trap.

Fourier transform techniques are also known to be used in orbital trapping electrostatic ion traps and FT-ICR mass spectrometers. According to these techniques, ions oscillate in a trapping field in a manner that is dependent on the mass to charge ratios of the ions. These oscillations are detected and the resulting signal is measured in the time domain. This signal is then converted to the frequency domain by using a Fourier transform to produce a mass spectrum. In these instruments, Fourier transformation of time domain data results in a complex frequency spectrum (i.e. comprising real and imaginary parts). For example, see Ref. J Am Soc Mass Spectrom. 2011 January; 22(1):138-47 Phase Correction of Fourier Transform Ion Cyclotron Resonance Mass Spectra Using MatLab.

When all signals have zero phase, the transformation from the measurement time-domain to the frequency-domain can be written as follows:

$$F(\omega)=\int F(t)e^{i\omega t}dt=A(\omega)+iD(\omega)$$

where $\omega$ is the characteristic frequency of the amplitude of the measured signal; $F(\omega)$ is the frequency domain data; $A(\omega)$ is the real part of the spectrum (absorption mode spectrum); and $D(\omega)$ is the imaginary part of the spectrum (dispersion mode spectrum).

In general, however, when signals have non-zero phases the real and imaginary parts of the frequency domain data can contain mixtures of the absorption and dispersion mode spectra. This may result in asymmetrical peak shapes for the real component after the Fourier transformation. In order to avoid such asymmetrical peak shapes it is known to use the phase-independent magnitude spectrum $M(\omega)$ of a Fourier transformation in order to determine the frequency and hence mass to charge ratios of the ions. The magnitude spectrum $M(\omega)$ is given by:

$$M(\omega)=[(A(\omega))^2+(D(\omega))^2]^{0.5}$$

The magnitude spectrum disregards phase information and so provides symmetrical peaks. However, the magnitude spectrum provides a relatively low resolution spectrum.

It is desired to provide an improved method of ion mobility spectrometry and an spectrometer therefor.

SUMMARY

From a first aspect the present invention provides a method of ion mobility spectrometry comprising:

transmitting ions to an ion mobility separator;

modulating the introduction of the ions into the ion mobility separator at a first modulation frequency;

separating the ions that enter the ion mobility separator according to ion mobility;

detecting ions that have exited the ion mobility separator with a detector;

wherein the transmission of ions from the ion mobility separator to the detector is modulated at a second modulation frequency, or the detector output is modulated at a second modulation frequency, such that the detector outputs a modulated signal;

varying the first and second modulation frequencies with time;

recording the intensity of the modulated signal as a function of the first or second modulation frequency so as to obtain data in a modulation frequency domain;

performing a Fourier transformation of said data so as to produce complex spectral data;

producing absorption spectral data representative of an absorption spectrum of said complex spectral data; and determining the ion mobilities of said ions from said absorption spectral data.

The use of the absorption spectrum to determine the ion mobility of the ions improves the resolution of drift time IMS data.

The inventors of the present invention have recognised that for FT-IMS techniques, the signals have the same starting phase and that the absorption mode spectrum can therefore be used to accurately determine the ion mobilities of the ions, without the peak shapes becoming asymmetrical after Fourier transformation.

Fundamentally, it has been recognised that when the frequency of the pulsing of the ion gates approaches zero (i.e. the ion gates remain open), the amplitude of the ion signal for ions of any ion mobility approaches a maximum. It therefore follows that the phases for all signals seen in the FT-IMS spectra are substantially identical. As the relationship between ion mobility and phase is known, $F(\omega)$ can be rotated in complex space to allow calculation of a pure absorption mode spectrum directly.

In FT-IMS systems the amplitude of the detected signal is measured with respect to the frequency of the gate signal ($\Omega$). For FT-IMS techniques, wherein all signals have the same starting phase, the relationship between the gate modulation frequency domain data and the complex spectral data is described by the following equation:

$$F(\omega) = \int F(\Omega) e^{i\omega\Omega} dt = A(\omega) + iD(\omega)$$

where $\omega$ is the characteristic frequency of the amplitude of the measured signal at the exit of the IMS device and $\Omega$ is the gate signal frequency; $F(\omega)$ is the ion signal as a function of IMS drift time; $A(\omega)$ is the real part of the spectrum (absorption mode spectrum); and $D(\omega)$ is the imaginary part of the spectrum (dispersion mode spectrum).

As discussed in the Background section, Knorr et al (Anal. Chem 1985) and Knorr et al (Anal. Chem 1986) disclose FT-IMS devices. However, there is no disclosure or suggestion in these techniques of determining the ion mobilities of the ions from said absorption spectral data. Rather, these techniques use the magnitude spectrum, which tends to provide a relatively low resolution spectrum.

Hieftje et al, Anal. Chem. Vol. 566, 28 Feb. 2006 "Phase-resolved detection in ion-mobility spectrometry", pages 45-54 discloses a method in which an ion entrance gate is modulated and wherein the frequency of modulation is varied with time. The ion mobility of an ion is determined from the phase of the detected signal relative to the modulation waveform. However, Hieftje et al does not disclose or suggest determining the ion mobilities of the ions from absorption spectral data. Furthermore, the technique of Hieftje et al is very different to the embodiments of the present invention, in that Hieftje et al only modulates a single ion gate and so provides a modulated signal for a given gate frequency. In contrast, according to embodiments of the present invention, both an ion entrance gate and an ion exit gate (or detector) is modulated so as to provide a constant signal for a given set of modulation frequencies that are then swept.

According to the present invention, at any given time the first frequency may be the same as the second frequency. The first and second frequencies may be varied together with time.

For the avoidance of doubt, it is pointed out that complex spectral data is data comprising both real components and imaginary components, i.e. a complex spectrum.

The step of determining the ion mobilities of said ions may comprise producing an ion mobility spectrum comprising said absorption spectrum.

The absorption spectrum may be the real part of the complex spectral data.

The method may comprise providing an ion entrance gate at the entrance of the ion mobility separator and applying an AC voltage to the ion entrance gate that periodically varies between a potential that blocks the transmission of ions into the ion mobility separator and a potential that permits ions to be transmitted into the ion mobility separator, wherein the frequency of the AC voltage is said first modulation frequency.

The detector output may be modulated at the second modulation frequency by electronics and/or software in the detector. For example, the detector may be a detector system including a data acquisition system and the data acquisition system may modulate the data that is recorded so as to produce the detector output that is modulated at the second modulation frequency. In other words, only some of the data may be recorded by the acquisition system.

Alternatively, or additionally, the method may comprise providing an ion exit gate at the exit of the ion mobility separator and applying an AC voltage to the ion exit gate that periodically varies between a potential that blocks the transmission of ions out of the ion mobility separator and a potential that permits ions to be transmitted out of the ion mobility separator, wherein the frequency of the AC voltage is said second modulation frequency.

The AC voltage applied to the ion entrance gate may be the same as the AC voltage applied to the ion exit gate at any given time.

The modulation frequency may be increased or decreased with time in a stepped manner, and a delay time may be provided after the modulation frequency is stepped to a new value.

The delay time left after each frequency step is selected so as to allow the ion signal exiting the ion mobility separator to reach a steady state.

Less desirably, the modulation frequency may be varied in a continuous manner.

The duty cycle of the ion entrance gate and/or ion exit gate may be 50%.

The method may comprise generating said ions. The ions may be generated by a continuous ion source and transmitted continuously to the ion mobility separator as a continuous ion beam.

The step of detecting ions may comprise measuring the amplitude of the ion signal output from the ion mobility separator.

The ion signal in the modulation frequency domain, for an ion of any given ion mobility, may vary periodically with a frequency that is characteristic of the ion mobility of that ion.

The method may comprise providing an ion mobility spectrum from said absorption spectral data, wherein the ion mobility spectrum represents the ion signal amplitude of the ions as a function of drift time through the ion mobility separator.

The method may comprise measuring the value of a parameter of the experimental environment or experimental conditions whilst varying the modulation frequency, wherein said parameter affects the modulation frequency domain signal or complex data, and correcting the modulation frequency domain signal or complex data based on the value of said parameter.

The parameter may be temperature or pressure of the experimental environment.

One or more calibrant ions may be analysed and the ion signal or complex data for other ions may be corrected based on the analysis of the calibrant ions.

The ion signals for ions of different ion mobilities all have the same phase according to the FT-IMS technique. However, the scenario is contemplated wherein the ion signals may have different phases. In such a scenario, the ion signals for ions having different ion mobilities have different phases and the method would comprise determining a phase function that is representative of the relationship between ion mobility and ion signal phase. The phase function may then be used to correct the phases for the ion signals. More specifically, the ion signals may be corrected to all have zero phase (i.e. no phase difference). Zero phase may be defined as being when the amplitude of the signal is either at its minimum or at its maximum at gate frequency of 0 Hz (or some other value). The use of a phase function to correct the data allows the absorption spectral data to be separated from the dispersion spectral data. Data corresponding to the absorption spectrum can then be obtained from the corrected data, without the absorption spectral data having a contribution from the dispersion spectrum, which would lead to asymmetry in the peak shapes. This is an improvement over known techniques such as the use of the magnitude spectrum, because the magnitude spectrum combines the real and imaginary parts of the Fourier transform and discards phase information, leading to broader peaks. The phase correction described above and the use of the absorption spectrum therefore provides the device with higher ion mobility resolution.

The method described above may comprise determining the phase function, for a given modulation frequency sweep, by analysing ions having known ion mobilities using the gated IMS device described herein so as to obtain ion signals for these ions as a function of gate voltage frequency for a range of gate voltage frequencies; extrapolating the ion signals for each ion of known ion mobility back to the point where the gate modulation frequency is 0 Hz (where it would be expected that for any ion the signal would be maximum at this point as the gates would be fully open at 0 Hz), or some other non-zero value; and determining the phase of each ion signal at the gate modulation frequency of 0 Hz (or said other value); and generating a phase function that relates the phase of the ion signal at the gate modulation frequency of 0 Hz (or said other value) to the ion mobilities of the known ions. The ion mobilities of unknown ions may subsequently be determined and the phase function may be used to determine the phases of the ion signals for these ions. This phase information may then be used to correct the data for the unknown ions so that ion signals for the ions have no phase difference and the method may then obtain a pure absorption spectrum.

The ions of known ion mobility may be calibrant ions introduced externally of the analyte, or may be calibrant ions forming part of said analyte. This method may comprise filtering, e.g. mass filtering, ions upstream of the ion mobility separator such that only said calibrant ions are introduced into the ion mobility separator for determining the phase function.

The first aspect of the present invention also provides an ion mobility spectrometer comprising:

an ion mobility separator for separating ions according to ion mobility;

a device for transmitting ions to the ion mobility separator;

a first modulator configured to modulate the introduction of ions into the ion mobility separator at a first modulation frequency;

an ion detector arranged for detecting ions that have exited the ion mobility separator;

a second modulator for modulating the transmission of ions from the ion mobility separator to the detector at a second modulation frequency, or for modulating an ion signal output from the detector at a second modulation frequency, such that the detector outputs a modulated signal; and a controller arranged and adapted to:

vary the first and second modulation frequency with time;

record the intensity of the modulated signal as a function of the first or second modulation frequency so as to obtain data in the modulation frequency domain;

perform a Fourier transformation of said data so as to produce complex spectral data;

produce absorption spectral data representative of an absorption spectrum of said complex spectral data; and determine the ion mobilities of said ions from said absorption spectral data.

The first modulator may be an ion entrance gate configured to modulate the introduction of ions into the ion mobility separator at the first modulation frequency; and/or the second modulator may be an ion exit gate configured to modulate the exiting of ions from the ion mobility separator to the detector at the second modulation frequency.

The spectrometer may comprise a mass analyser for mass analysing the ions downstream of the ion mobility separator. Alternatively, or additionally, the spectrometer may comprise a mass analyser for mass analysing the ions upstream of the ion mobility separator. Said mass analysing may be performed by providing a mass filter upstream of the ion mobility separator and mass selectively transmitting ions of known mass to charge ratio to the ion mobility separator.

The spectrometer may be arranged and configured with a controller for performing any of the methods described herein.

For example, the spectrometer may be configured to be operated such that at any given time the first frequency may be the same as the second frequency. The spectrometer may be configured to vary the first and second frequencies together with time.

The spectrometer may be configured to determine the ion mobilities of the ions from ion mobility spectral data comprising said absorption spectrum.

The absorption spectrum may be the real part of the complex spectral data.

The spectrometer may comprise an ion entrance gate at the entrance of the ion mobility separator and a device for applying an AC voltage to the ion entrance gate that periodically varies between a potential that blocks the transmission of ions into the ion mobility separator and a potential that permits ions to be transmitted into the ion mobility separator, wherein the frequency of the AC voltage is said first modulation frequency. Alternatively, or additionally, the spectrometer may comprise an ion exit gate at the exit of the ion mobility separator and a device for applying an AC voltage to the ion exit gate that periodically varies between a potential that blocks the transmission of ions out of the ion mobility separator and a potential that permits ions to be transmitted out of the ion mobility separator, wherein the frequency of the AC voltage is said second modulation frequency.

The spectrometer may be configured such that the AC voltage applied to the ion entrance gate is the same as the AC voltage applied to the ion exit gate at any given time.

The spectrometer may be configured to increase or decrease the modulation frequency with time in a stepped manner, and such that a delay time is provided after the modulation frequency is stepped to a new value.

The delay time left after each frequency step may be selected so as to allow the ion signal exiting the ion mobility separator to reach a steady state.

Less desirably, the spectrometer may be configured to vary the modulation frequency in a continuous manner.

The spectrometer may be configured such that the duty cycle of the ion entrance gate and/or ion exit gate is 50%.

The spectrometer may comprise an ion source for generating said ions, or ions from which said ions are derived. The ion source may be a continuous ion source and the ions may be transmitted continuously to the ion mobility separator as a continuous ion beam.

The ion detector may be configured to measure the amplitude of the ion signal output from the ion mobility separator.

The controller may be configured to provide an ion mobility spectrum (or ion mobility spectral data) from said absorption spectral data; wherein the ion mobility spectrum (or spectral data) represents (or is representative of) the ion signal amplitude of the ions as a function of drift time through the ion mobility separator.

The spectrometer may comprise a sensor for measuring the value of a parameter of the experimental environment or experimental conditions whilst varying the modulation frequency, wherein said parameter affects the modulation frequency domain signal or complex data, and the controller may be configured to correct the modulation frequency domain signal or complex data based on the value of said parameter.

The parameter may be temperature or pressure of the experimental environment.

The second modulation is performed downstream of the ion mobility separator.

Accordingly, from a second aspect the invention provides a method of ion mobility spectrometry comprising:

transmitting ions to an ion mobility separator;

modulating the introduction of the ions into the ion mobility separator at a first modulation frequency;

separating the ions that enter the ion mobility separator according to ion mobility;

detecting ions that have exited the ion mobility separator with a detector;

applying a modulation downstream of the ion mobility separator at a second modulation frequency so as to cause a modulation in data recorded from the detector so as to obtain modulated data in a modulation frequency domain; wherein the first and second modulation frequencies are varied with time;

performing a Fourier transformation of said modulated data so as to produce complex spectral data;

producing absorption spectral data representative of an absorption spectrum of said complex spectral data; and determining the ion mobilities of said ions from said absorption spectral data.

This method may comprise any of the features described in relation to the first aspect, except wherein the second modulation is performed by the more general step of applying a modulation downstream of the ion mobility separator at a second modulation frequency so as to cause the modulation in the data recorded from the detector.

For example, the second modulation frequency may be selected to be maintained at the same modulation frequency as the first modulation frequency whilst the first and second modulation frequencies are varied.

The method may be operated such that there is no mixing of ions between the ion mobility separator and the detector.

The second aspect of the invention also provides an ion mobility spectrometer comprising:

an ion mobility separator for separating ions according to ion mobility;

a device for transmitting ions to the ion mobility separator;

a first modulator configured to modulate the introduction of ions into the ion mobility separator at a first modulation frequency;

an ion detector arranged for detecting ions that have exited the ion mobility separator; and a controller arranged and adapted to:

apply a modulation downstream of the ion mobility separator at a second modulation frequency so as to cause a modulation in data recorded from the detector so as to obtain modulated data in a modulation frequency domain; wherein the first and second modulation frequencies are varied with time;

perform a Fourier transformation of said modulated data so as to produce complex spectral data;

produce absorption spectral data representative of an absorption spectrum of said complex spectral data; and determine the ion mobilities of said ions from said absorption spectral data.

This spectrometer may comprise any of the features described in relation to the first aspect, except wherein the second modulation is performed by the more general step of applying a modulation downstream of the ion mobility separator at a second modulation frequency so as to cause the modulation in the data recorded from the detector.

The spectrometer disclosed herein may comprise:

(a) an ion source selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; (xviii) a Thermospray ion source; (xix) an Atmospheric Sampling Glow Discharge Ionisation ("ASGDI") ion source; (xx) a Glow Discharge ("GD") ion source; (xxi) an Impactor ion source; (xxii) a Direct Analysis in Real Time ("DART") ion source; (xxiii) a Laserspray Ionisation ("LSI") ion source; (xxiv) a Sonicspray Ionisation ("SSI") ion source; (xxv) a Matrix Assisted Inlet Ionisation ("MAII") ion source; (xxvi) a Solvent Assisted Inlet Ionisation ("SAII") ion source; (xxvii) a Desorption Electrospray Ionisation ("DESI") ion source; and (xxviii) a Laser Ablation Electrospray Ionisation ("LAESI") ion source; and/or (b) one or more continuous or pulsed ion sources; and/or (c) one or more ion guides; and/or (d) one or more ion mobility separation devices and/or one or more Field Asymmetric Ion Mobility Spectrometer devices; and/or (e) one or more ion traps or one or more ion trapping regions; and/or (f) one or more collision, fragmentation or reaction cells selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionisation Dissociation ("EID") fragmentation device; and/or (g) a mass analyser selected from the group consisting of: (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic mass analyser arranged to generate an electrostatic field having a quadro-logarithmic potential distribution; (x) a Fourier Transform electrostatic mass analyser; (xi) a Fourier Transform mass analyser; (xii) a Time of Flight mass analyser; (xiii) an orthogonal acceleration Time of Flight mass analyser; and (xiv) a linear acceleration Time of Flight mass analyser; and/or (h) one or more energy analysers or electrostatic energy analysers; and/or (i) one or more ion detectors; and/or (j) one or more mass filters selected from the group consisting of: (i) a quadrupole mass filter; (ii) a 2D or linear quadrupole ion trap; (iii) a Paul or 3D quadrupole ion trap; (iv) a Penning ion trap; (v) an ion trap; (vi) a magnetic sector mass filter; (vii) a Time of Flight mass filter; and (viii) a Wien filter; and/or (k) a device or ion gate for pulsing ions; and/or (l) a device for converting a substantially continuous ion beam into a pulsed ion beam.

The spectrometer may comprise an electrostatic ion trap or mass analyser that employs inductive detection and time domain signal processing that converts time domain signals to mass to charge ratio domain signals or spectra. Said signal processing may include, but is not limited to, Fourier Transform, probabilistic analysis, filter diagonalisation, forward fitting or least squares fitting.

The spectrometer may comprise either:

(i) a C-trap and a mass analyser comprising an outer barrel-like electrode and a coaxial inner spindle-like electrode that form an electrostatic field with a quadro-logarithmic potential distribution, wherein in a first mode of operation ions are transmitted to the C-trap and are then injected into the mass analyser and wherein in a second mode of operation ions are transmitted to the C-trap and then to a collision cell or Electron Transfer Dissociation device wherein at least some ions are fragmented into fragment ions, and wherein the fragment ions are then transmitted to the C-trap before being injected into the mass analyser; and/or (ii) a stacked ring ion guide comprising a plurality of electrodes each having an aperture through which ions are transmitted in use and wherein the spacing of the electrodes increases along the length of the ion path, and wherein the apertures in the electrodes in an upstream section of the ion guide have a first diameter and wherein the apertures in the electrodes in a downstream section of the ion guide have a second diameter which is smaller than the first diameter, and wherein opposite phases of an AC or RF voltage are applied, in use, to successive electrodes.

The spectrometer may comprise a device arranged and adapted to supply an AC or RF voltage to the electrodes. The AC or RF voltage may have an amplitude selected from the group consisting of: (i) <50 V peak to peak; (ii) 50-100 V peak to peak; (iii) 100-150 V peak to peak; (iv) 150-200 V peak to peak; (v) 200-250 V peak to peak; (vi) 250-300 V peak to peak; (vii) 300-350 V peak to peak; (viii) 350-400 V peak to peak; (ix) 400-450 V peak to peak; (x) 450-500 V peak to peak; and (xi) >500 V peak to peak.

The AC or RF voltage may have a frequency selected from the group consisting of: (i) <100 kHz; (ii) 100-200 kHz; (iii) 200-300 kHz; (iv) 300-400 kHz; (v) 400-500 kHz; (vi) 0.5-1.0 MHz; (vii) 1.0-1.5 MHz; (viii) 1.5-2.0 MHz; (ix) 2.0-2.5 MHz; (x) 2.5-3.0 MHz; (xi) 3.0-3.5 MHz; (xii) 3.5-4.0 MHz; (xiii) 4.0-4.5 MHz; (xiv) 4.5-5.0 MHz; (xv) 5.0-5.5 MHz; (xvi) 5.5-6.0 MHz; (xvii) 6.0-6.5 MHz; (xviii) 6.5-7.0 MHz; (xix) 7.0-7.5 MHz; (xx) 7.5-8.0 MHz; (xxi) 8.0-8.5 MHz; (xxii) 8.5-9.0 MHz; (xxiii) 9.0-9.5 MHz; (xxiv) 9.5-10.0 MHz; and (xxv) >10.0 MHz.

The spectrometer may comprise a chromatography or other separation device upstream of an ion source. According to an embodiment the chromatography separation device comprises a liquid chromatography or gas chromatography device. According to another embodiment the separation device may comprise: (i) a Capillary Electrophoresis ("CE") separation device; (ii) a Capillary Electrochromatography ("CEC") separation device; (iii) a substantially rigid ceramic-based multilayer microfluidic substrate ("ceramic tile") separation device; or (iv) a supercritical fluid chromatography separation device.

The ion guide may be maintained at a pressure selected from the group consisting of: (i) <0.0001 mbar; (ii) 0.0001-0.001 mbar; (iii) 0.001-0.01 mbar; (iv) 0.01-0.1 mbar; (v) 0.1-1 mbar; (vi) 1-10 mbar; (vii) 10-100 mbar; (viii) 100-1000 mbar; and (ix) >1000 mbar.

Analyte ions may be subjected to Electron Transfer Dissociation ("ETD") fragmentation in an Electron Transfer Dissociation fragmentation device. Analyte ions may be caused to interact with ETD reagent ions within an ion guide or fragmentation device.

Optionally, in order to effect Electron Transfer Dissociation either: (a) analyte ions are fragmented or are induced to dissociate and form product or fragment ions upon interacting with reagent ions; and/or (b) electrons are transferred from one or more reagent anions or negatively charged ions to one or more multiply charged analyte cations or positively charged ions whereupon at least some of the multiply charged analyte cations or positively charged ions are induced to dissociate and form product or fragment ions; and/or (c) analyte ions are fragmented or are induced to dissociate and form product or fragment ions upon interacting with neutral reagent gas molecules or atoms or a non-ionic reagent gas; and/or (d) electrons are transferred from one or more neutral, non-ionic or uncharged basic gases or vapours to one or more multiply charged analyte cations or positively charged ions whereupon at least some of the multiply charged analyte cations or positively charged ions are induced to dissociate and form product or fragment ions; and/or (e) electrons are transferred from one or more neutral, non-ionic or uncharged superbase reagent gases or vapours to one or more multiply charged analyte cations or positively charged ions whereupon at least some of the multiply charge analyte cations or positively charged ions are induced to dissociate and form product or fragment ions; and/or (f) electrons are transferred from one or more neutral, non-ionic or uncharged alkali metal gases or vapours to one or more multiply charged analyte cations or positively charged ions whereupon at least some of the multiply charged analyte cations or positively charged ions are induced to dissociate and form product or fragment ions; and/or (g) electrons are transferred from one or more neutral, non-ionic or uncharged gases, vapours or atoms to one or more multiply charged analyte cations or positively charged ions whereupon at least some of the multiply charged analyte cations or positively charged ions are induced to dissociate and form product or fragment ions, wherein the one or more neutral, non-ionic or uncharged gases, vapours or atoms are selected from the group consisting of: (i) sodium vapour or atoms; (ii) lithium vapour or atoms; (iii) potassium vapour or atoms; (iv) rubidium vapour or atoms; (v) caesium vapour or atoms; (vi) francium vapour or atoms; (vii) $C_{60}$ vapour or atoms; and (viii) magnesium vapour or atoms.

The multiply charged analyte cations or positively charged ions may comprise peptides, polypeptides, proteins or biomolecules.

Optionally, in order to effect Electron Transfer Dissociation: (a) the reagent anions or negatively charged ions are derived from a polyaromatic hydrocarbon or a substituted polyaromatic hydrocarbon; and/or (b) the reagent anions or negatively charged ions are derived from the group consisting of: (i) anthracene; (ii) 9,10 diphenyl-anthracene; (iii) naphthalene; (iv) fluorine; (v) phenanthrene; (vi) pyrene; (vii) fluoranthene; (viii) chrysene; (ix) triphenylene; (x) perylene; (xi) acridine; (xii) 2,2' dipyridyl; (xiii) 2,2' biquinoline; (xiv) 9-anthracenecarbonitrile; (xv) dibenzothiophene; (xvi) 1,10'-phenanthroline; (xvii) 9' anthracenecarbonitrile; and (xviii) anthraquinone; and/or (c) the reagent ions or negatively charged ions comprise azobenzene anions or azobenzene radical anions.

The process of Electron Transfer Dissociation fragmentation may comprise interacting analyte ions with reagent ions, wherein the reagent ions comprise dicyanobenzene, 4-nitrotoluene or azulene reagent ions.

BRIEF DESCRIPTION OF THE DRAWINGS

Embodiments of the present invention will now be described, by way of example only, and with reference to the accompanying drawings in which.

DETAILED DESCRIPTION

Figure 1:
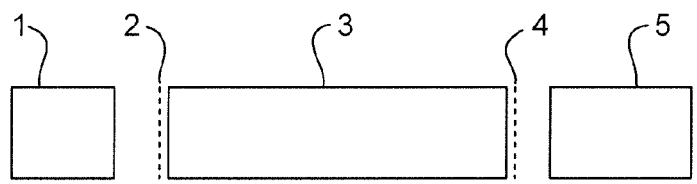
FIG. 1 shows a schematic of an FT-IMS instrument according to an embodiment of the invention.

FIG. 1 shows a schematic of an FT-IMS device according to an embodiment of the invention. The instrument comprises a continuous ion source 1, an entrance ion gate 2, an IMS device 3, an exit ion gate 4 and an ion analyser 5. During operation the ion source 1 supplies a continuous beam of ions towards the IMS device 3. Electrical potentials are applied to the entrance ion gate 2 so as to periodically allow ions to enter the IMS device 3 and periodically block ions from entering the IMS device 3. Ions that are permitted to enter the IMS device 3 by the ion gate 2 are caused to separate in the IMS device 3 according to their ion mobility through a gas in the IMS device 3. Electrical potentials are applied to the exit ion gate 4 so as to periodically block ions from exiting the IMS device 3 and periodically allow ions to exit the IMS device 3. The ions that exit the IMS device 3 through the exit ion gate 4 are transmitted to one or more downstream analysers 5 that analyse, process and detect the ions.

In order to periodically block and transmit ions, each of the entrance and exit ion gates 2,4 may be supplied with an AC voltage. The same AC voltage may be applied to both of the ion gates 2,4. When the AC voltage is high, ions are blocked by the ion gates 2,4 and when the AC voltage is low, ions are permitted to be transmitted through the ion gates 2,4. The frequency of the voltage applied to each of the ion gates 2,4 is swept with time and the ion signal leaving the IMS device 3 is measured by the analyser 5 as a function of the frequency of the voltage applied to the ion gates 2,4. The same frequency voltage may be applied to the ion gates 2,4. It should be noted that although it is preferable to apply the same frequency of voltage to both ion gates, different frequencies could be applied. However, this may result in a more complex amplitude oscillation with more than one oscillation frequency for individual ion mobilities and so would require more complex processing to determine ion mobility.

The amplitude of the ion signal output from the IMS device 3, for an ion of any given ion mobility, varies as a substantially triangular function having a frequency that is characteristic of the ion mobility of the ion. This data, representing the ion signal amplitude obtained in the frequency domain of the ion gate voltage, is then Fourier transformed so as to produce an ion mobility separation spectrum that represents the ion signal amplitude as a function of IMS drift time.

A simple mathematical model was produced in order to illustrate the advantages of the present invention. According to this model, five ion species of different relative intensities and different drift times through the IMS device 3 are considered. The first ion species (#1) has a drift time of 9.85 ms and a relative intensity of 0.1. The second ion species (#2) has a drift time of 10 ms and a relative intensity of 1.0. The third ion species (#3) has a drift time of 10.2 ms and a relative intensity of 0.7. The fourth ion species (#4) has a drift time of 10.4 ms and a relative intensity of 0.7. The fifth ion species (#5) has a drift time of 10.6 ms and a relative intensity of 0.50.

According to this model, the ion gates 2,4 were supplied with a square wave AC voltage having a 50% duty cycle. The frequency of the voltage was stepped from 1 Hz to 20 kHz in steps of 10 Hz. During operation, time must be left after each voltage frequency step in order to allow the ion signal exiting the exit ion gate 4 to reach a steady state. For the ion species modelled, a delay of at least 10.6 ms should be left between each frequency step. As such, the total analysis time would be 21 seconds.

In order to emulate the effects of diffusive broadening, the width of the ion packet gated into the IMS device 3 by entrance ion gate 2 was convolved with a Gaussian arrival time distribution having a standard deviation of 30 microseconds.

Figure 2:
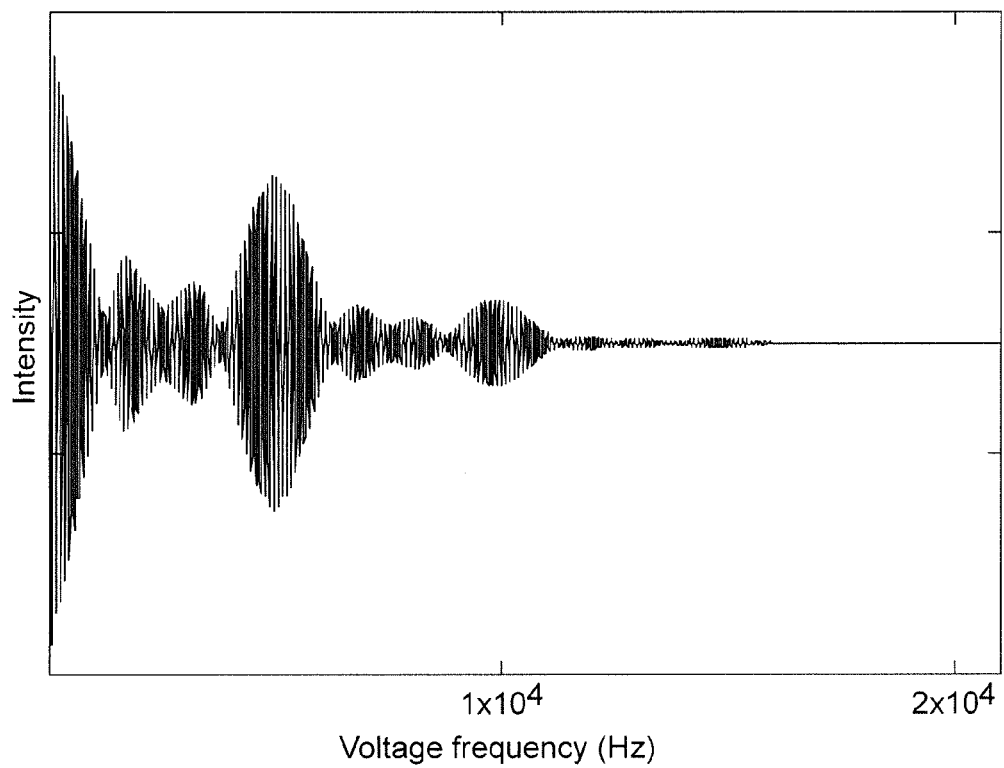
FIG. 2 shows the ion signal measured by the instrument of FIG. 1 in the gate voltage frequency domain.

FIG. 2 shows a plot of ion signal intensity detected by analyser 5 as a function of the frequency, in Hz, of the voltage applied to the ion gates 2,4 for the mixture of the five ions species modelled above.

Figure 3:
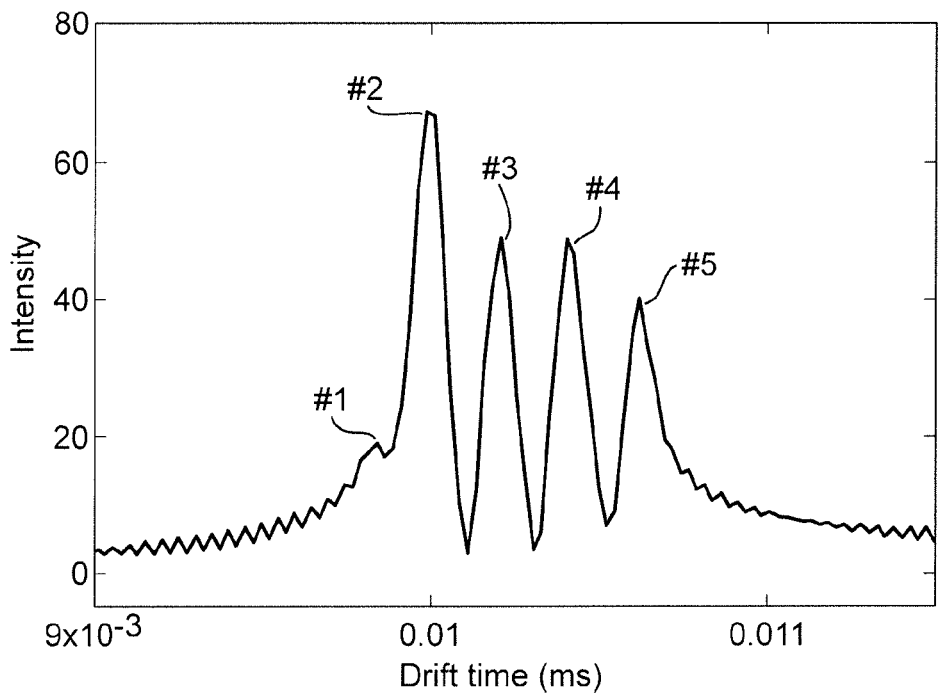
FIG. 3 shows an IMS spectrum obtained by a technique not according to the present invention, by taking a magnitude mode Fourier transform of the data in FIG. 2.

FIG. 3 shows a Fourier transform of the data in FIG. 2 using a known technique that uses the magnitude mode. The magnitude spectrum is given by:

$$M(\omega)=[(A(\omega))^2+(D(\omega))^2]^{0.5}$$

FIG. 3 shows the intensity of the ion signal as a function of drift time through the IMS device 3. The IMS spectrum includes a peak corresponding to each of the five ion species (#1 to #5) modelled. These peaks are labelled in FIG. 3 with their respective ion species.

Figure 4:
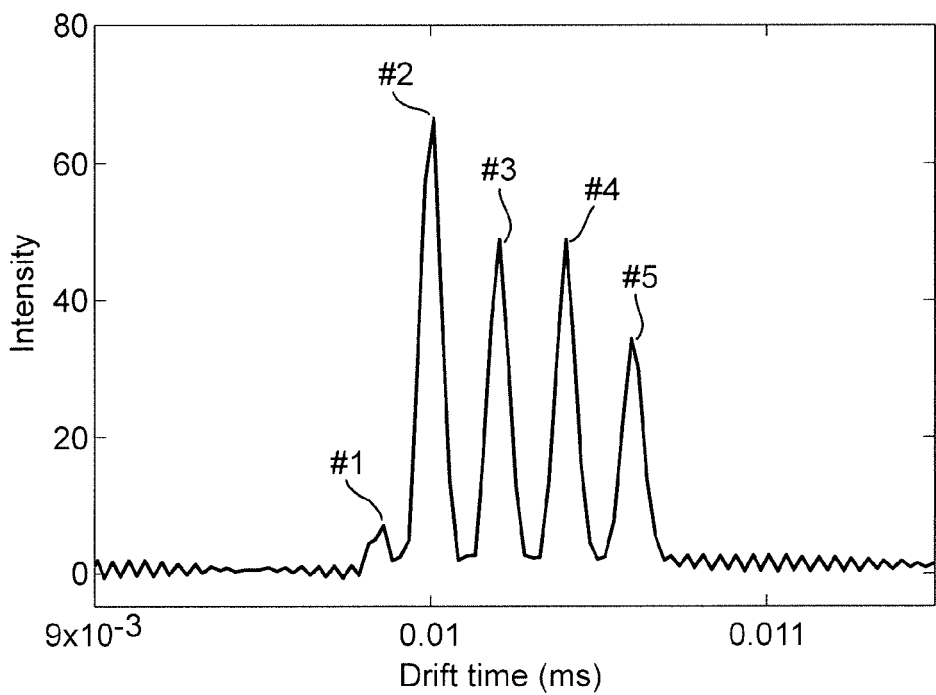
FIG. 4 shows an IMS spectrum obtained according to an embodiment of the present invention by taking an absorption mode Fourier transform of the data in FIG. 2.

FIG. 4 shows a Fourier transform of the data in FIG. 2 according to an embodiment of the present invention that uses the absorption mode. The absorption mode spectrum was calculated by assuming that the phase of the oscillation of the signal was identical for each ion species. FIG. 4 shows the intensity of the ion signal as a function of drift time through the IMS device 3. The IMS spectrum includes a peak corresponding to each of the five ion species (#1 to #5) modelled. The peaks are labelled in FIG. 4 with their respective ion species.

By comparing FIG. 3 with FIG. 4, it can be seen that the absorption mode IMS data according to the embodiment of the present invention and shown in FIG. 4 has higher resolution and better peak shape than the magnitude mode IMS data of the prior art and shown in FIG. 3. More specifically, the low and high drift time tails of each peak are substantially reduced in FIG. 4 and the peaks are resolved nearly to the baseline (i.e. to a signal intensity of almost zero). The minor intensity peak of ion species #1 at drift time 9.85 ms is clearly resolved according to the absorption mode method of FIG. 4, whereas it appears as an indistinct shoulder in the magnitude mode method of FIG. 3.

As described above, the inventors of the present invention have recognised that, theoretically, all of the signals recorded using the FT-IMS device have the same phase and that therefore no phase correction is required in order to calculate and use the absorption mode spectrum to accurately determine the ion mobilities of the ions. However, It is recognised that variations in pressure, temperature or other changes in the experimental environment during the frequency scan of the voltage applied to the ion gates may result in distortions of the ideal signal. This may prevent the accurate calculation of the IMS spectrum. For example, a change in temperature or pressure may result in a time-dependent stretching of the data obtained in the ion gate voltage frequency domain. The data may be corrected (prior to being Fourier transformed or subjected to other data processing techniques) using information from gauges or sensors, or by using internal standards.

For example, the FT-IMS instrument may be coupled with a mass spectrometer and an internal standard having a known mass to charge ratio may be used to obtain a pure signal at the known mass to charge ratio. The pure signal may then be extracted and used to determine the necessary correction to the data due to changes in the environmental conditions. The internal standard may, for example, be any sufficiently pure species present in the analyte.

Although the phases of the signals in an FT-IMS technique are substantially the same, the situation is contemplated wherein there might, in practice, be some small phase differences between the signals. In such a scenario, a phase function may be determined and phase correction may be required. For a given ion gate modulation frequency sweep, the phase function may be determined by examining the frequency and phase of the ion signal for specific species of ions having known mass to charge ratios and/or known ion mobilities. A set of ion species having no interferences may be examined. This may be performed by only introducing a set of ion species having no interferences into the FT-IMS device, or by identifying a set of ion species having no interference in the analyte. These species may then be used as calibration standards.

Data from multiple species may be examined in order to produce a best fit phase function, which relates the phase of an ion signal to the frequency of the ion signal. The phase function may then be used in subsequent analysis to correct the phase for all of the components of the ion signal, thereby producing an absorption spectrum with higher IMS resolution.

Although the FT-IMS device has been described as being coupled with a mass spectrometer, this is not essential.

Although the present invention has been described with reference to various embodiments, it will be understood by those skilled in the art that various changes in form and detail may be made without departing from the scope of the invention as set forth in the accompanying claims.

The invention claimed is:
1. A method of ion mobility spectrometry comprising:
transmitting ions to an ion mobility separator;
modulating the introduction of the ions into the ion mobility separator at a first modulation frequency;
separating the ions that enter the ion mobility separator according to ion mobility;
detecting ions that have exited the ion mobility separator with a detector;
wherein the transmission of ions from the ion mobility separator to the detector is modulated at a second modulation frequency, or the detector output is modulated at a second modulation frequency, such that the detector outputs a modulated signal;
varying the first and second modulation frequencies with time;
recording the intensity of the modulated signal as a function of the first or second modulation frequency so as to obtain data in a modulation frequency domain;
performing a Fourier transformation of said data so as to produce complex spectral data;
producing absorption spectral data representative of an absorption spectrum of said complex spectral data; and
determining the ion mobilities of said ions from said absorption spectral data.

2. The method of claim 1, wherein at any given time the first frequency is the same as the second frequency, and wherein the first and second frequencies are varied together with time.

3. The method of claim 1, wherein the absorption spectrum is the real part of the complex spectral data.

4. The method of claim 1, comprising providing an ion entrance gate at the entrance of the ion mobility separator and applying an AC voltage to the ion entrance gate that periodically varies between a potential that blocks the transmission of ions into the ion mobility separator and a potential that permits ions to be transmitted into the ion mobility separator, wherein the frequency of the AC voltage is said first modulation frequency; and/or providing an ion exit gate at the exit of the ion mobility separator and applying an AC voltage to the ion exit gate that periodically varies between a potential that blocks the transmission of ions out of the ion mobility separator and a potential that permits ions to be transmitted out of the ion mobility separator, wherein the frequency of the AC voltage is said second modulation frequency.

5. The method of claim 4, wherein the AC voltage applied to the ion entrance gate is the same as the AC voltage applied to the ion exit gate at any given time.

6. The method of claim 1, wherein the modulation frequency is increased or decreased with time in a stepped manner, and wherein a delay time is provided after the modulation frequency is stepped to a new value.

7. The method of claim 1, wherein said ion signal in the modulation frequency domain, for an ion of any given ion mobility, varies periodically with a frequency that is characteristic of the ion mobility of that ion.

8. The method of claim 1, comprising providing an ion mobility spectrum from said absorption spectral data, wherein the ion mobility spectrum represents the ion signal amplitude of the ions as a function of drift time through the ion mobility separator.

9. The method of claim 1, comprising measuring the value of a parameter of the experimental environment or experimental conditions whilst varying the modulation frequency, wherein said parameter affects the modulation frequency domain signal or complex data, and correcting the modulation frequency domain signal or complex data based on the value of said parameter.

10. The method of claim 9, wherein the parameter is temperature or pressure of the experimental environment.

11. The method of claim 1, wherein one or more calibrant ions are analysed and the ion signal or complex data for other ions is corrected based on the analysis of the calibrant ions.

12. An ion mobility spectrometer comprising:
an ion mobility separator for separating ions according to ion mobility;
a device for transmitting ions to the ion mobility separator;
a first modulator configured to modulate the introduction of ions into the ion mobility separator at a first modulation frequency;
an ion detector arranged for detecting ions that have exited the ion mobility separator;
a second modulator for modulating the transmission of ions from the ion mobility separator to the detector at a second modulation frequency, or for modulating an ion signal output from the detector at a second modulation frequency, such that the detector outputs a modulated signal; and
a controller arranged and adapted to:
vary the first and second modulation frequency with time;
record the intensity of the modulated signal as a function of the first or second modulation frequency so as to obtain data in the modulation frequency domain;
perform a Fourier transformation of said data so as to produce complex spectral data;
produce absorption spectral data representative of an absorption spectrum of said complex spectral data; and
determine the ion mobilities of said ions from said absorption spectral data.

13. The spectrometer of claim 12, wherein said first modulator is an ion entrance gate configured to modulate the introduction of ions into the ion mobility separator at the first modulation frequency; and/or wherein said second modulator is an ion exit gate configured to modulate the exiting of ions from the ion mobility separator to the detector at the second modulation frequency.

14. A method of ion mobility spectrometry comprising:
transmitting ions to an ion mobility separator;
modulating the introduction of the ions into the ion mobility separator at a first modulation frequency;
separating the ions that enter the ion mobility separator according to ion mobility;
detecting ions that have exited the ion mobility separator with a detector;
applying a modulation downstream of the ion mobility separator at a second modulation frequency so as to cause a modulation in data recorded from the detector so as to obtain modulated data in a modulation frequency domain; wherein the first and second modulation frequencies are varied with time;;
performing a Fourier transformation of said modulated data so as to produce complex spectral data;
producing absorption spectral data representative of an absorption spectrum of said complex spectral data; and
determining the ion mobilities of said ions from said absorption spectral data.

15. An ion mobility spectrometer comprising:
an ion mobility separator for separating ions according to ion mobility;
a device for transmitting ions to the ion mobility separator;
a first modulator configured to modulate the introduction of ions into the ion mobility separator at a first modulation frequency;
an ion detector arranged for detecting ions that have exited the ion mobility separator; and
a controller arranged and adapted to:
apply a modulation downstream of the ion mobility separator at a second modulation frequency so as to cause a modulation in data recorded from the detector so as to obtain modulated data in a modulation frequency domain; wherein the first and second modulation frequencies are varied with time;
perform a Fourier transformation of said modulated data so as to produce complex spectral data;
produce absorption spectral data representative of an absorption spectrum of said complex spectral data; and
determine the ion mobilities of said ions from said absorption spectral data.

* * * * *